United States Patent
Bae et al.

(10) Patent No.: US 7,947,222 B2
(45) Date of Patent: May 24, 2011

(54) MOBILE COMMUNICATION TERMINAL EQUIPPED WITH TEMPERATURE COMPENSATION FUNCTION FOR USE IN BIO-INFORMATION MEASUREMENT

(75) Inventors: Byeong-woo Bae, Anyang-si (KR); Sung-dong Lee, Yeongcheon-si (KR); Hong-seong Suk, Anyang-si (KR); Jina Yoo, Anyang-si (KR); Ki-won Lee, Pocheon-si (KR)

(73) Assignee: Infopia Co., Ltd. (KR)

( * ) Notice: Subject to any disclaimer, the term of this patent is extended or adjusted under 35 U.S.C. 154(b) by 918 days.

(21) Appl. No.: 11/504,505

(22) Filed: Aug. 15, 2006

(65) Prior Publication Data
US 2010/0259394 A1    Oct. 14, 2010

(51) Int. Cl.
*C12Q 1/68* (2006.01)
*G01N 27/327* (2006.01)
*H04M 1/38* (2006.01)
*G08B 1/08* (2006.01)

(52) U.S. Cl. ........... 422/50; 204/403.02; 204/403.11; 204/403.01; 204/403.1; 455/556.1; 340/539.15; 422/402

(58) Field of Classification Search ........ 204/403.01–403.15; 422/55–58, 422/50, 402; 340/539.15; 455/556.1
See application file for complete search history.

(56) References Cited

U.S. PATENT DOCUMENTS

| | | | |
|---|---|---|---|
| 5,232,667 A * | 8/1993 | Hieb et al. | 422/82.04 |
| 5,405,511 A | 4/1995 | White et al. | |
| 6,493,069 B1 | 12/2002 | Nagashimada et al. | |
| 6,753,187 B2 * | 6/2004 | Cizdziel et al. | 436/169 |
| 6,787,109 B2 * | 9/2004 | Haar et al. | 422/82.05 |
| 6,880,968 B1 | 4/2005 | Haar | |
| 2005/0019848 A1 | 1/2005 | Lee et al. | |
| 2005/0272468 A1 | 12/2005 | Tsai et al. | |

FOREIGN PATENT DOCUMENTS

| CN | 1662173 | 8/2005 |
|---|---|---|
| WO | WO 9922236 A1 * | 5/1999 |

OTHER PUBLICATIONS

European Search Report; EP 06017069; Feb. 12, 2007 All references cited in the Search Report and not previously submitted are listed above.
First Notification of Office Action; The State Intellectual Property Office of P.R. China; 200610111634.X; May 22, 2009, All references cited in the Foreign Office Actin and not previously submitted are listed above.
European Office Action for Application No. 06017069.3 mailed Sep. 9, 2010.

* cited by examiner

*Primary Examiner* — Alex Noguerola
(74) *Attorney, Agent, or Firm* — Cantor Colburn LLP

(57) ABSTRACT

Disclosed is a mobile communication terminal equipped with temperature compensation function for use in bio-information measurement, including a biosensor insertion in which a biosensor directly detecting bio-information of a subject is inserted, a temperature measurement unit measuring temperatures, and a controller analyzing the bio-information inputted from the biosensor based on stored analysis data and correcting the bio-information using the temperature measured by the temperature measurement unit, in which the temperature measurement unit measures temperature of a target object without contacting the target object directly.

4 Claims, 4 Drawing Sheets

MOBILE COMMUNICATION TERMINAL EQUIPPED WITH TEMPERATURE COMPENSATION FUNCTION FOR USE IN BIO-INFORMATION MEASUREMENT

BACKGROUND OF THE INVENTION

1. Field of the Invention

The present invention relates to a mobile communication terminal equipped with temperature compensation function for use in bio-information measurement.

2. Description of Related Art

A biosensor is device for the detection of an analyte that combines a biological component with a physicochemical detector component.

The biosensor is a biochemical sensor that selectively detects and measures chemical substances contained in samples and, in particular, detects organic compounds, such as specific constituents of enzymes or antibodies or microbes, which are sensitive to specific matters. The biochemical sensor is utilized to detect and measure organic compounds that are difficult to detect by means of non-biochemical sensors that have been used until now.

A first sensing mechanism of the biosensor is as follows.

The biosensor detects organisms, such as specific constituents of enzymes or antibodies or microbes, by means of a sensing element and converts the amount (or concentration) of chemical substances detected by the sensing element into voltage or current values by means of transducers and electrodes.

In addition, the biosensor may be classified into an enzyme sensor, a microbial sensor, and an immunity sensor. The enzyme sensor and microbial sensor are currently put to use. The most widespread example of a commercial biosensor is the enzyme sensor, which uses singularities of enzyme proteins acting only on specific substrate molecules or responses.

Examples of the enzyme sensor developed or currently utilized include a glucose sensor for detecting blood glucose for patients suffering from diabetes, a urea sensor used as a blood urea concentration sensor for hemodialysis control of a bioartificial kidney, and a uric acid sensor used as a blood uric acid concentration sensor for patients suffering from gout. In addition, there has been developed a multifunctional enzyme sensor detecting the concentrations of two or more chemical substances at the same time. An example of the multifunctional enzyme sensor is a freshness sensor that determines the freshness of fish or meat by measuring the concentrations of three or more chemical substances at the same time.

The microbial sensor is used in process management of fermentation industries such as alcohol fermentation and glutamic acid fermentation, or in measurement of BOD (Biochemical Oxygen Demand) that is an index of water pollution. In addition, even though lower in sensitivity than the microbial sensor, a biosensor using a large organism such as fish has been studied.

The immunity sensor using antibodies as a sensing element is used in disease diagnosis. For instance, recently there has been developed an immunity sensor equipped with an antibody corresponding to a marker peculiar to cancer as a sensing element. The immunity sensor may be used in early detection of AIDS (Acquired Immune Deficiency Syndrome).

Recently there has been developed a small-sized semiconductor biosensor equipped with a thin-film shaped enzyme on a small semiconductor chip. If the semiconductor biosensor is put to practical use, it can be inserted to organisms to directly measure the constituent parts of blood and other components, and the simultaneous measurement of a plurality of chemical substances can be carried out more easily and quickly.

A sensing mechanism of the biosensor is as follows.

The biosensor irradiates a predetermined range of wavelength on a target object by spectroscopic method, analyzes a reflected wavelength, and compares it with a predetermined data table. Different ranges of wavelengths are used depending on the types of target object.

When organism information is measured with the biosensor, blood glucose levels, cholesterol levels, and hepatic metabolite levels are greatly affected by temperatures. Accordingly, the temperature needs to be compensated for accurate measurements.

Blood glucose measurement based on the above-mentioned first mechanism has the following features.

Since blood glucose levels of patients suffering from glucosuria keep changing due to excessive exercise, food and drink, and complications, they need to keep monitoring the blood glucose levels. There are various kinds of blood glucose monitors, such as medical devices for monitoring blood glucose levels, and mobile phones equipped with blood glucose monitors.

FIG. 1 is a mobile communication terminal equipped with a conventional blood glucose monitor.

A biosensor 1 applied with enzyme responding to blood glucose is inserted into a biosensor insertion 5 of a battery pack 2 in a mobile communication terminal 10 equipped with a blood glucose monitor. The mobile communication terminal 10 measures blood glucose levels by means of a main body 8 and displays the levels on a display unit 9.

Korean Patent Application Publication No. 2003-96652 discloses a mobile communication terminal equipped with a conventional blood glucose monitor. According to the publication, after inserting a strip sensor applied with enzyme reacting with glucose into a mobile communication terminal, blood is injected into the strip sensor. Alternatively, after injecting blood into the strip sensor applied with the enzyme reacting with glucose, the strip sensor is inserted into the mobile communication terminal. The glucose and enzyme react with each other on the strip sensor, creating electrons. The electrons are detected by a current sensor. The current sensor detects current flowing through two terminals, and converts the current into digital signals so as to be appropriate for an input terminal of a mobile station modem (MSM). When the digital signals are input to the MSM, the digital signals are processed based on data (relationship of current/voltage based on reagent codes) stored in a memory unit, and are displayed as blood glucose levels on a liquid crystal display (LCD) device.

However, since the reaction between the glucose and the enzyme in the mobile communication terminal is sensitive to temperatures, there are the following problems:

First, it is not possible to measure blood glucose levels since the mobile communication terminal cannot keep its temperature constant due to heat generated from the mobile communication terminal itself.

Secondly, it is not possible to measure blood glucose levels since the reaction temperature between the glucose and enzyme cannot be detected.

SUMMARY OF THE INVENTION

The present invention provides a mobile communication terminal equipped with temperature compensation function for use in bio-information measurement, which measures reaction temperature between glucose and enzyme reacting with the glucose and corrects blood glucose levels measured on the mobile communication terminal based on the reaction temperature, and accurately measures bio-information, such as blood glucose levels, that is affected by temperatures.

According to an aspect of the present invention, there is provided a mobile communication terminal equipped with temperature compensation function for use in bio-information measurement, including a biosensor insertion in which a biosensor directly detecting bio-information of a subject is inserted, a temperature measurement unit measuring temperatures, and a controller analyzing the bio-information inputted from the biosensor based on stored analysis data and correcting the bio-information using the temperature measured by the temperature measurement unit, in which the temperature measurement unit measures temperature of a target object without contacting the target object directly.

The mobile communication terminal equipped with temperature compensation function for use in bio-information measurement according to the present invention uses a non-contact temperature sensor to measure the temperature of biosensor housing, and corrects bio-information, such as blood glucose levels, cholesterol levels, and hepatic metabolite levels, that is affected by temperatures.

The biosensor may be applied with enzymes reacting with glucose, cholesterol, hepatic metabolite and the like.

The enzyme reacting with glucose may be glucose oxidase and glucose dehydrogenase.

The temperature measurement unit may be a non-contact temperature sensor.

The non-contact temperature sensor may be an infrared temperature sensor.

The mobile communication terminal equipped with temperature compensation function for use in bio-information measurement can be used to correct cholesterol levels when a cholesterol measurement biosensor is used instead of the glucose measurement biosensor.

The mobile communication terminal equipped with temperature compensation function for use in bio-information measurement can be used to correct hepatic metabolite levels when a hepatic metabolite measurement biosensor is used instead of the glucose measurement biosensor.

A method of measuring bio-information using the mobile communication terminal equipped with temperature compensation function for use in bio-information measurement according to the present invention includes measuring the temperature of biosensor housing with a non-contact temperature sensor incorporated in the mobile communication terminal, and using the temperature as an enzyme reaction temperature to correct values in a data table based on the enzyme reaction temperature.

A method of measuring blood glucose using the mobile communication terminal equipped with temperature compensation function for use in bio-information measurement according to the present invention may further include returning to operation of determining whether or not a bio-information measurement mode (blood glucose measurement mode) is selected after general functions of the mobile communication terminal are carried out.

The amount of blood may be 1 to 10 μl.

A method of correcting cholesterol levels may be the same as that of correcting the blood glucose levels except that a cholesterol sensor is used instead of the glucose sensor.

A method of correcting hepatic metabolite levels may be the same as that of correcting the blood glucose levels except that a hepatic metabolite sensor is used instead of the glucose sensor.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Exemplary embodiments in accordance with the present invention will now be described in detail with reference to the accompanying drawings.

Figure 1:
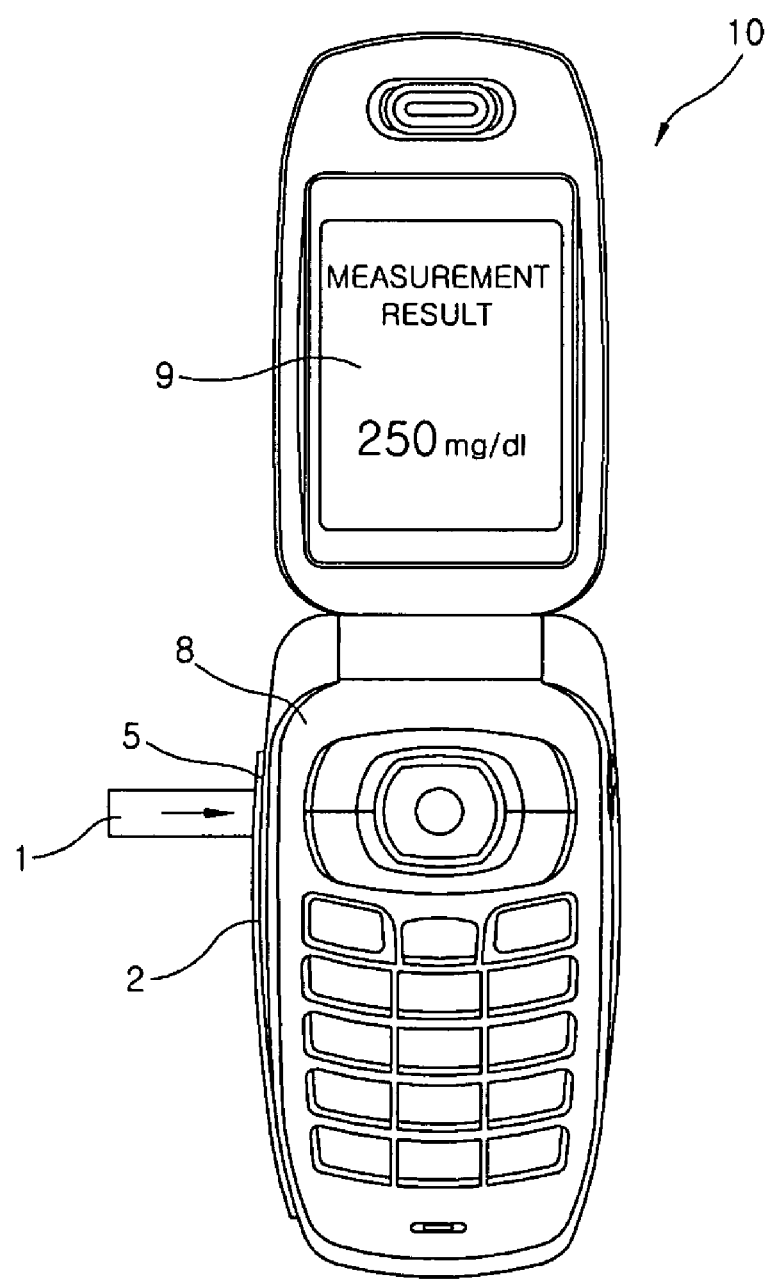
FIG. 1 is a mobile communication terminal equipped with a conventional blood glucose monitor.
Figure 2:
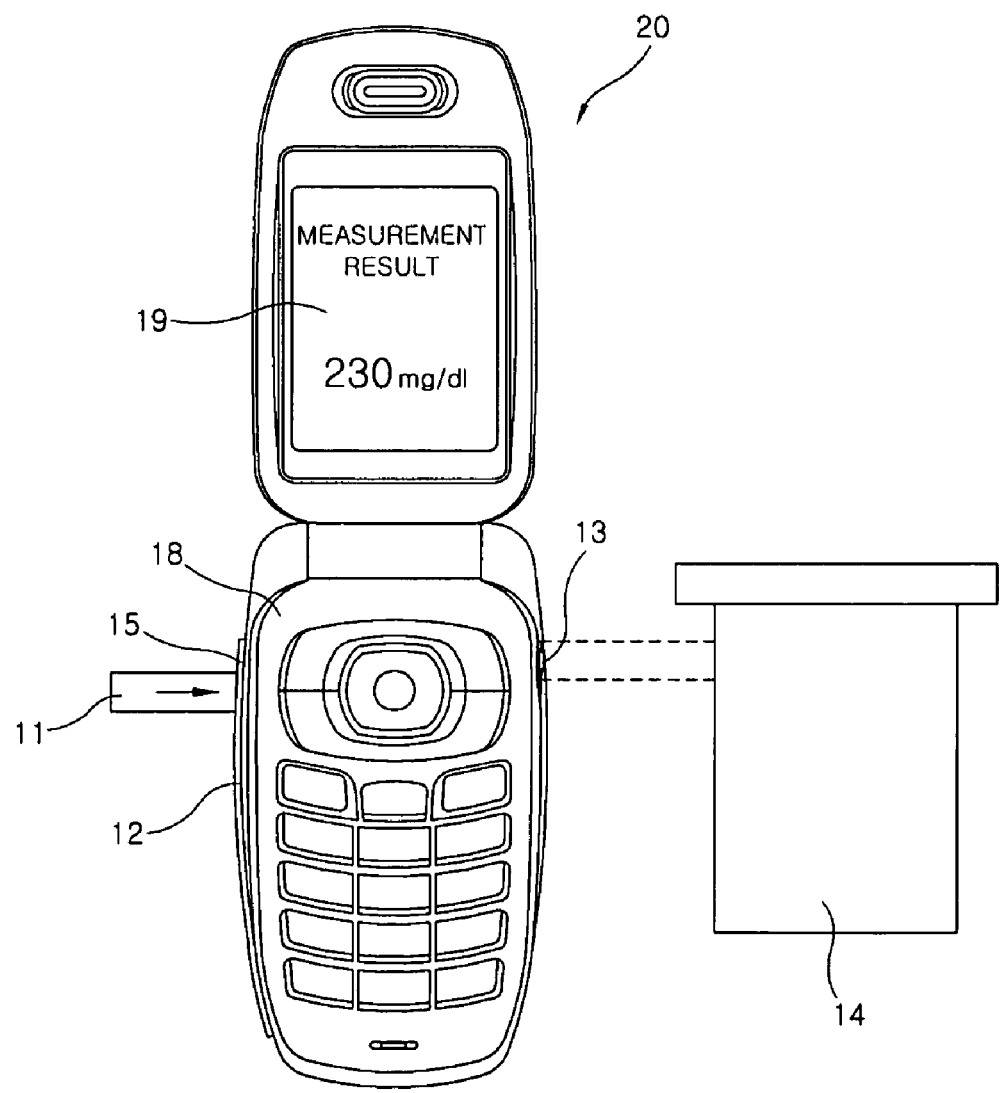
FIG. 2 is a mobile communication terminal equipped with temperature compensation function for use in bio-information measurement according to an embodiment of the present invention.

FIG. 2 is a mobile communication terminal equipped with temperature compensation function for use in bio-information measurement according to an embodiment of the present invention.

A mobile communication terminal 20 equipped with a monitor for measuring blood glucose levels, cholesterol levels, and hepatic metabolite levels measures temperature of a biosensor housing 14 with a non-contact temperature sensor 13. The non-contact temperature sensor 13 is preferably an infrared sensor.

A biosensor 11 is inserted into a biosensor insertion 15 in a battery pack 12. A main body 18 of the mobile communication terminal 20 corrects its temperature to the temperature of the biosensor housing 14, measures the blood glucose levels, cholesterol levels, and hepatic metabolite levels, and displays measurement results on a display unit 19.

Figure 3:
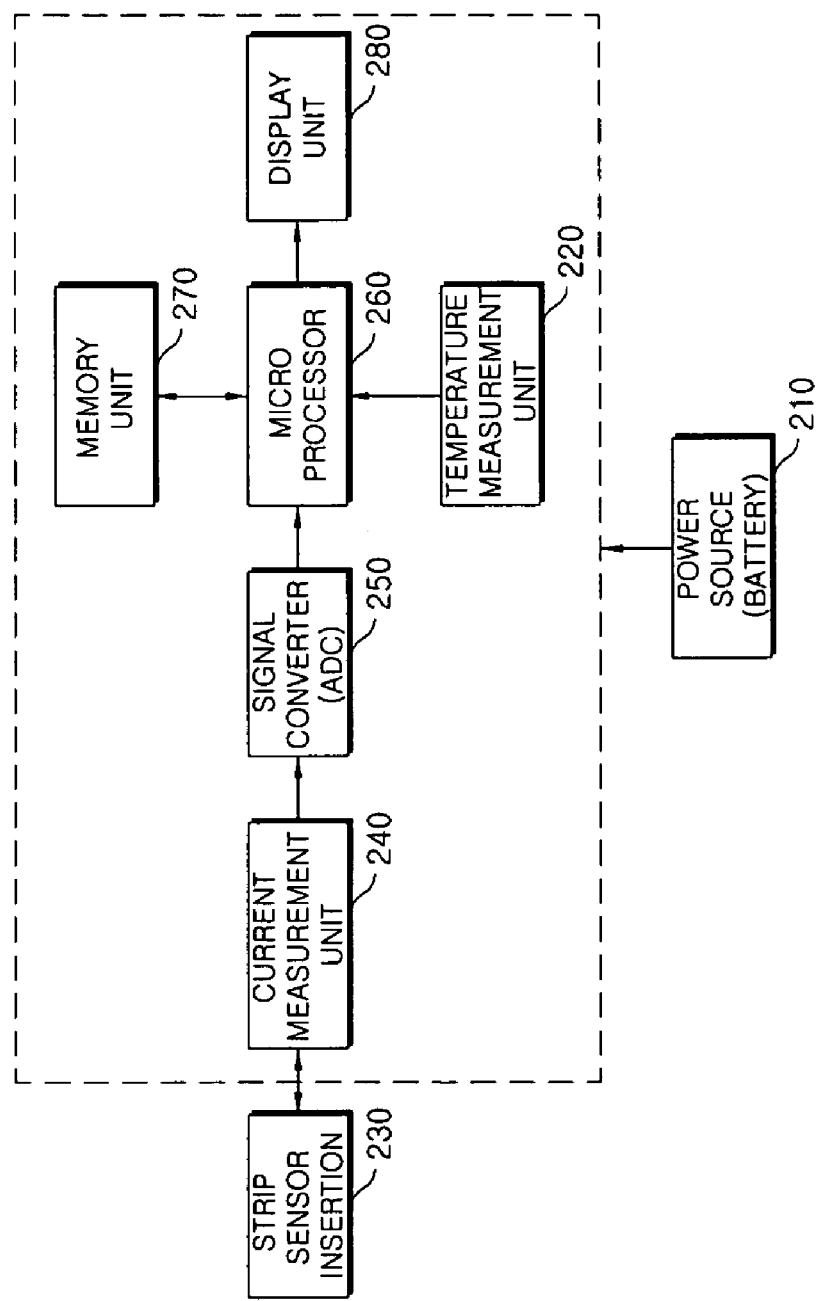
FIG. 3 is a block diagram of a mobile communication terminal equipped with temperature compensation function for use in bio-information measurement according to an embodiment of the present invention.

FIG. 3 is a block diagram of a mobile communication terminal equipped with temperature compensation function for use in bio-information measurement according to an embodiment of the present invention.

A power source 210 supplies power to a bio-information measurement unit using the temperature-compensated mobile communication terminal. The power source 210 mainly uses a battery.

A temperature measurement unit 220 is a non-contact one, and measures the temperature of a strip sensor housing.

A strip sensor having a bio-information detector is inserted into the mobile communication terminal through a strip sensor insertion 230.

A current measurement unit 240 receives the power, has two terminals, and detects variations in current based on the concentration of target materials between the two terminals.

A signal converter (ADC) 250 converts the detected current to digital signals.

The bio-information may be detected by a spectroscopic method instead of the electrochemical method. The spectroscopic method includes irradiating a predetermined range of wavelength on a target object, analyzing a reflected wavelength, comparing it with a predetermined data table, and determining the target object. The predetermined range of wavelength varies depending on the types of target object.

A microprocessor 260 receives the digital signal, and outputs a control signal to receive the data table and obtain concentration data of the target materials from the digital signal.

A memory unit 270 stores data table concerning reagent codes and relationship between current/voltage based on temperatures, and outputs the data table to the microprocessor 260 according to the control signal from the microprocessor 260.

A display unit 280 of the mobile communication terminal receives the concentration data from the microprocessor 260 and displays the concentration data.

Figure 4:
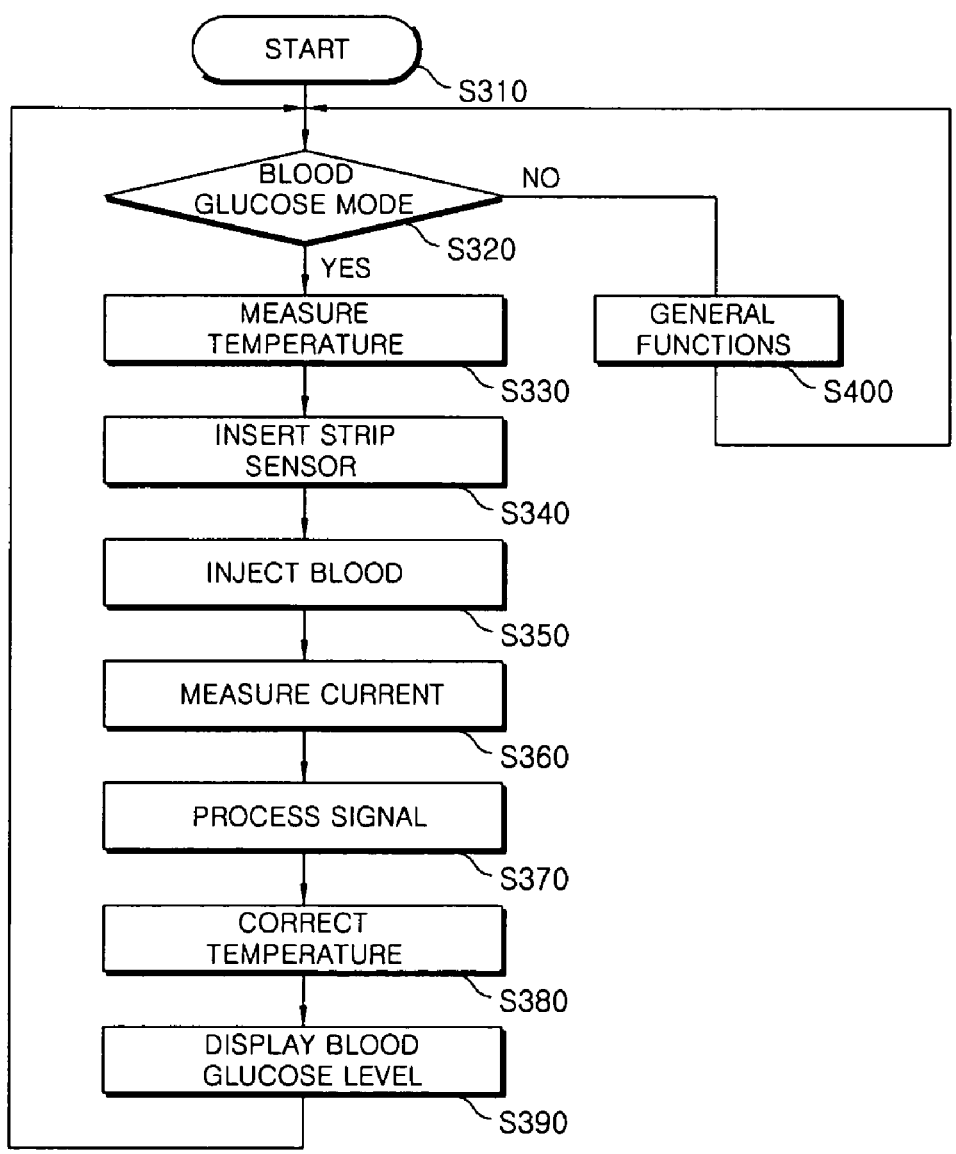
FIG. 4 is a flow chart of a mobile communication terminal equipped with temperature compensation function for use in bio-information measurement according to an embodiment of the present invention.

FIG. 4 is a flow chart of a mobile communication terminal equipped with temperature compensation function for use in bio-information measurement according to an embodiment of the present invention.

After operating the mobile communication terminal (S310), it is determined whether or not the mobile communication terminal is in a blood glucose measurement mode (S320). If it is not in the blood glucose measurement mode, the mobile communication terminal carries out general functions (S400).

The temperature of the strip sensor housing is measured with the non-contact temperature sensor (S330).

The strip sensor is inserted into the strip sensor insertion of the mobile communication terminal (S340).

Blood is collected and injected to the strip sensor (S350).

Current is detected between the two terminals by electrons created by reaction between glucose (blood glucose) and glucose oxidase (S360).

The detected current is converted to a digital signal (S370).

Concentration data indicating blood glucose levels is acquired from the digital signal and the data table compensated to the temperature of the strip sensor housing (S380).

The concentration data is displayed on the display unit (S390).

After that, it returns to the operation S320 in which it is determined whether or not the mobile communication terminal is in the blood glucose measurement mode.

When the blood glucose measurement mode is not selected, the mobile communication terminal carries out the general functions (S400), and returns to the operation S320.

A method of measuring and correcting cholesterol levels and hepatic metabolite levels is the same as the method of measuring and correcting the blood glucose levels except that a cholesterol sensor and a hepatic metabolite sensor are used to measure the cholesterol levels and hepatic metabolite levels, respectively.

As apparent from the above description, since the mobile communication terminal equipped with temperature compensation function for use in bio-information measurement measures temperatures with a non-contact temperature sensor and compensates for the temperature for bio-information measurement of the mobile communication terminal, it is possible to accurately measure various types of bio materials that are sensitive to temperature.

While the present invention has been described with reference to exemplary embodiments thereof, it will be understood by those skilled in the art that various changes in form and details may be made therein without departing from the scope of the present invention as defined by the following claims.

What is claimed is:

1. A mobile communication terminal equipped with temperature compensation function for use in bio-information measurement, including
    a biosensor insertion into which a biosensor directly detecting bio-information of a subject is inserted,
    a temperature measurement unit measuring temperatures, and
    a controller analyzing the bio-information inputted from the biosensor based on stored analysis data and correcting the bio-information using the temperature measured by the temperature measurement unit,
    wherein the temperature measurement unit measures temperatures of a biosensor housing without contacting the biosensor housing directly and with the biosensor completely outside the biosensor housing, and
    wherein the controller corrects the bio-information using the temperature of the biosensor housing measured by the temperature measurement unit.

2. The mobile communication terminal of claim 1, wherein the biosensor includes glucose oxidase or glucose dehydrogenase.

3. The mobile communication terminal of claim 1, wherein the temperature measurement unit is a non-contact temperature sensor.

4. The mobile communication terminal of claim 3, wherein the non-contact temperature sensor is an infrared temperature sensor.

* * * * *